US00PP34211P2

(12) United States Plant Patent
Sheehan

(10) Patent No.: US PP34,211 P2
(45) Date of Patent: May 10, 2022

(54) GRAPEVINE PLANT NAMED 'SHEEGENE 28'

(50) Latin Name: *Vitis vinifera*
Varietal Denomination: Sheegene 28

(71) Applicant: Sheehan Genetics, LLC, Fresno, CA (US)

(72) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 0 days.

(21) Appl. No.: 17/197,842

(22) Filed: Mar. 10, 2021

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206, 207
See application file for complete search history.

(56) References Cited

U.S. PATENT DOCUMENTS

PP4,787 P 11/1981 Olmo et al.
PP26,527 P2 3/2016 Ramming et al.

*Primary Examiner* — Susan McCormick Ewoldt
(74) *Attorney, Agent, or Firm* — Dentons US LLP

(57) ABSTRACT

'Sheegene 28' is a new and distinct grapevine plant with novel characteristics that include small to medium-sized green (2.5 GY 8/8) seedless grape with a very good flavor for use as a table grape and in raisin production. The 'Sheegene 28' harvesting period for fresh fruit is the third week of June while the harvesting period for raisins is mid- to late-July, in the San Joaquin Valley of California.

1 Drawing Sheet

Latin name of the genus and species of the plant claimed: *Vitis vinifera.*

Variety denomination: 'Sheegene 28'.

BACKGROUND OF THE INVENTION

The present invention relates to a new and distinct variety of seedless grapevine named 'Sheegene 28'. 'Sheegene 28' produces small to medium-sized, green, seedless grapes on bunches for use as a table grape or in raisin production. The new variety was first hybridized by Timothy P. Sheehan of Porterville, Calif., as a cross of 'Flame' (not patented), as the pollen parent, and 'Red Globe' (U.S. Plant Pat. No. 4,787), as the seed parent, in 2000. The new variety was asexually propagated in the dormant season of 2004, grafted on 'Harmony' (not patented), virus free rootstock, in a *Vitis vinifera* variety block located near Fowler, Calif. The berry size is small to medium but with very good flavor and matures at least four weeks before 'Thompson Seedless'. All characteristics and distinctions remain true to form and are established and transmitted through succeeding propagations.

SUMMARY OF THE INVENTION

The following are the most outstanding and distinguishing characteristics of 'Sheegene 28'. 'Sheegene 28' produces small to medium-sized green (2.5 GY 8/8) seedless grape with a very good flavor and matures for harvesting and shipping in the third week of June in the San Joaquin Valley of Central California. The new variety most closely resembles 'Thompson Seedless' (not patented) but differs in maturity. Specifically, 'Sheegene 28' matures at least four weeks before 'Thompson Seedless' with a sweet and very good flavor. 'Sheegene 28' produces berries of 2 grams for fresh grapes and about 0.5 gram for Raisin grapes. Clusters weight about 454 grams. The variety is ideally suited for producing raisins by allowing grapes to wilt and naturally dry on the vine, or by cutting canes in mid- to late-July to accelerate drying, or by a combination of natural drying and cutting canes. In the San Joaquin Valley, 'Sheegene 28' fruit reaches full maturity by mid- to late-July with 21° Brix or more. Production potential is high and estimated at 20 Tn/hectare for fresh grapes and 4 to 5 Tn/hectare for dry grapes. Raisin quality is excellent with good sensory qualities and similar appearance to 'Thompson Seedless' (not patented). The new variety is similar to USDA variety 'Sunpreme' (U.S. Plant Pat. No. 26,527), in that fruit naturally begins to wilt by late-July and then dries to a raisin by mid-October.

The new variety is distinguished from its male parent, 'Flame' (not patented) in that 'Sheegene 28' produces green-colored grapes while 'Flame' produces red colored grapes.

'Sheegene 28' is distinguished from its female parent, 'Red Globe' (U.S. Plant Pat. No. 4,787), in that the new variety produces green seedless grapes, as compared to its seed parent 'Red Globe' (U.S. Plant Pat. No. 4,787), that produces seeded grapes.

'Sheegene 28' matures four to five weeks earlier than all other commercial raisin varieties including 'Fiesta' (not patented), 'Selma Pete' (not patented), 'Thompson Seedless', 'Flame Seedless' (not patented), and 'Supreme'. On July 30, the sugar concentration for 'Sheegene 28' was 26° Brix compared to 17° Brix for 'Thompson Seedless', 19° Brix for 'Flame Seedless', 18° Brix for 'Sunpreme', and 19° Brix for 'Selma Pete'—all vineyards sampled located in close proximity.

Veraison is early for the 'Sheegene 28' variety when compared to other raisin varieties. On June 19, the 'Sheegene 28' was at 100% berry softening compared to 0% for 'Thompson Seedless', 5% for 'Flame Seedless', 30% for 'Sunpreme', and 1% for 'Selma Pete'.

Bloom is also earlier for the 'Sheegene 28' variety. On May 1, 'Sheegene 28' was at 80% bloom; whereas, bloom had not started in any of the other varieties. All comparisons described above were made in the San Joaquin Valley of California.

An unusual characteristic of 'Sheegene 28' is the absence of secondary clusters even though the variety has plenty of lateral shoots.

BRIEF DESCRIPTION OF THE DRAWING

FIG. 1—Shows the form, foliage, and fruit of a 4-year-old 'Sheegene 28' vine grown in the field in Fresno, Calif. The colors shown are as true as can be reasonably obtained by conventional photographic procedures.

DETAILED BOTANICAL DESCRIPTION

The following detailed description sets forth the distinctive characteristics of 'Sheegene 28'. The detailed description was obtained between March and November using 4-year-old plants grown in the field in California, USA. The color references are to the *Munsell Color Charts for Plant Tissue,* 1977 Edition by Munsell Color.

Classification:
- *Family*.—Vitaceae.
- *Botanical name*.—*Vitis vinifera.*
- *Common name*.—Grapevine.
- *Variety name*.—'Sheegene 28'.

Plant:
- *Plant habit and growth*.—Semi-erect, lateral shoots plentiful but no secondary clusters.
- *Age at maturity*.—4 years.
- *Size* (*at maturity*).—Height (at maturity): 220 cm. Width (at maturity): 300 cm.
- *Vigor*.—Med-high.
- *Productivity*.—High.
- *Rootstock*.—'Freedom' rootstock grafted in nursery.

Trunk:
- *Size*.—Diameter: 6 cm measured 35 cm above ground. Surface texture: Rough.
- *Color*.—Exterior, 5YR 5/2; Interior, 2.5 YR 4/6.

Canes:
- *Size*.—Diameter: 1.5 cm measured at 5th node. Length: 210 cm.
- *Surface texture* (*mature cane*).—Finely ribbed.
- *Surface texture* (*immature cane*).—Very finely ribbed.
- *Form* (*woody shoot cross section form*).—Pith in center with diaphragm at nodes.
- *Color* (*mature*).—Color and indicate specific age: 7 months, 7.5 YR 6/8.
- *Color* (*immature*).—4 weeks, 7.5 GY 7/6.
- *Internode length* (*upper mature sun cane*).—13.5 cm.

*Time of bud burst*.—50% bud burst on March 5.

Tendrils:
- *Form*.—Mostly trifid.
- *Size*.—Large.
- *Length*.—27 cm on average.
- *Diameter*.—3.5 mm measured at middle of tendril.
- *Texture and distribution of tendril at each node beginning at base*.—Smooth with very slight ribs toward base, 0000010110110110 (0 means no tendril at that node and 1 means there is tendril at the node).
- *Color* (*mature*).—2 weeks 5 GY 6/6.
- *Anthocynanin* (*mature*).—Absent.
- *Color* (*immature*).—4 days, 5 GY 6/4.
- *Anthocynanin* (*immature*).—Absent.

Growing tips (young shoot):
- *Pubescence*.—Slight cottony.
- *Color*.—2.5 GY 6/6.
- *Anthocyanin*.—Present 2.5 YR 6/8.
- *Shape*.—Fully Open.
- *Apex*.—Triangular.

Leaves:
- *Shape*.—Cuneiform.
- *Apex*.—Pointed.
- *Base*.—Rounded.
- *Margin*.—Erose.
- *Length of teeth on margin*.—4 to 10 mm, average=7 mm.
- *Shape of teeth on margin*.—Irregular, both sides convex.
- *Texture* (*mature leaf*).—Upper surface: Slight puckering along veins. Lower surface: Slight puckering along veins.
- *Size*.—Immature, length: 1 week, average 10 cm. Immature, width: 1 week, average 10 cm. Mature, length: 2.5 weeks, average 19.5 cm. Mature, width: 2.5 weeks, average 19 cm.
- *Color, immature leaf*.—Upper surface: 5 GY 6/8. Lower surface: 5 GY 6/8.
- *Color, mature leaf*.—Upper surface: 5 GY 4/6. Lower surface: 5 GY 5/6.
- *Venation*.—Pattern: veins on upper surface are flat; veins on lower surface are raised. Color: Upper surface: 5 GY 7/6. Lower surface: 5 GY 7/6.
- *Petiolar sinus*.—Slightly open to half open.
- *Petiole*.—Length: 10.5 cm on average. Diameter: 3.5 mm on average. Color: 5 GY 6/6.

Floral cluster:
- *General description and location*.—Cluster are long, carrot shaped. About half of the clusters have a large wing that sticks out horizontally.
- *Quantity of inflorescences per cluster*.—520 per cluster on average.
- *Size*.—Length: 23 cm on average. Width: 16 cm wide on average.
- *Peduncle*.—Length: 3.2 cm on average.
- *Inflorescences*.—Hermaphroditic.
- *Stamens*.—Upright; straight to slightly angled; medium length.
- *Anthers*.—General description: not distinct, small.
- *Date of bloom*.—80% bloom on May 1.
- *Pollen amount*.—Moderate.
- *Calyptra*.—Insert general description 5 segments, complete separation.
- *Calyptra color*.—5GY 5/6.

Fruit:
- *Time of year of commercial harvest and shipment*.—July 15 to August 1.
- *Cluster* (*primary bunches*).—Generally, size: Medium to large; 392 g. Length (without peduncle): 23 cm. Width: hanging, 12 cm. Density: Medium. Peduncle length: 3 cm. Peduncle diameter: 5.5 mm. Peduncle color: 2.5 GY 6/8. Number of berries per cluster: 200.

*Berry*.—Size: Small to medium (2 g/berry). Shape: Almost round. Uniformity: Medium. Brix content: 24° Brix on August 1. Size: Diameter: 14 mm. Length: 16 mm. Skin color: 2.5 GY 8/8. Pedicel: Length: 10 mm. Diameter: 1 mm. Color: 5 GY 5/8. Strength of attachment to berry: medium.

*Cluster* (*secondary bunches*).—No secondary clusters found.

Berry flesh:

*Color*.—2.5 GY 8/6.

*Juice, color*.—Clear.

*Juice production*.—Medium.

*Thickness of skin*.—Medium.

*Flavor*.—Neutral.

*Fragrance*.—None detected.

*Texture*.—Soft, juicy.

*Seeds*.—No seeds.

*Use*.—Fresh, table grape; raisins.

Disease and insect resistance: This cultivar is susceptible to the main diseases of its species, such as *Erysiphe necator, Plasmopara viticola, Botrytis cinerea, Daktulosphaira vifoliae, Ceratitis capitata, Planococcus ficus, Planococcus citri, Empoasca vitis*.

What is claimed is:

1. A new and distinct variety of grapevine called 'Sheegene 28' as shown and described herein.

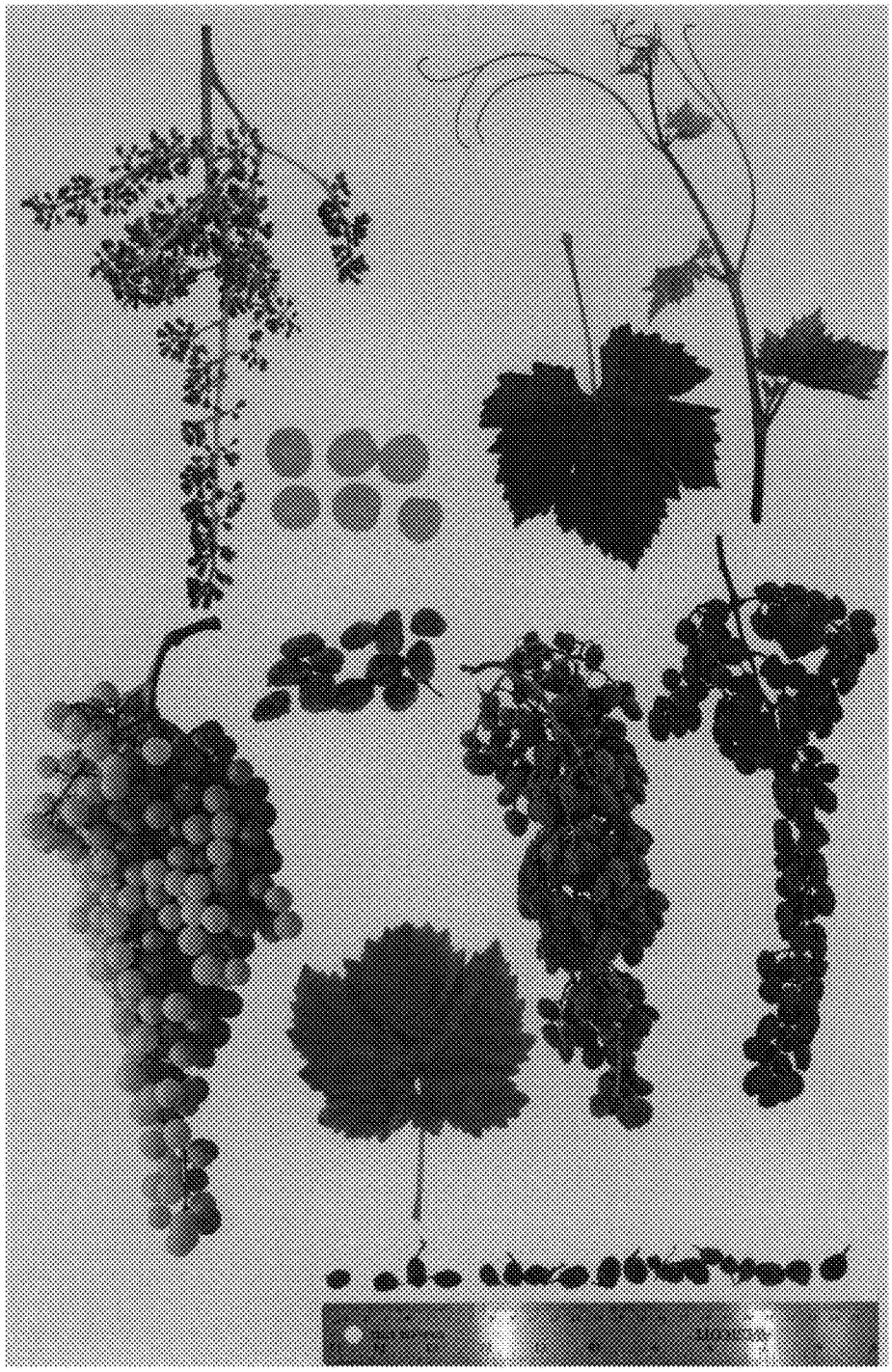

* * * * *